United States Patent [19]

Imonti et al.

[11] Patent Number: 4,784,649
[45] Date of Patent: Nov. 15, 1988

[54] SURGICAL ASPIRATOR CANNULA

[75] Inventors: Maurice M. Imonti, Dana Point; Charles E. Beuchat, Irvine, both of Calif.

[73] Assignee: The Cooper Companies, Inc., Menlo Park, Calif.

[21] Appl. No.: 28,504

[22] Filed: Mar. 20, 1987

[51] Int. Cl.⁴ ............................................. A61M 5/325
[52] U.S. Cl. ...................... 604/240; 285/38; 604/119
[58] Field of Search ............... 604/119, 120, 118, 140, 604/146, 147, 149, 151, 152, 153, 240–243, 187, 902, 35; 285/38; 128/229

[56] References Cited

U.S. PATENT DOCUMENTS

| | | | |
|---|---|---|---|
| 1,520,508 | 12/1924 | Platt et al. | 604/241 |
| 3,071,402 | 9/1959 | Lasto et al. | 604/902 |
| 3,461,870 | 8/1969 | Linge | 604/118 |
| 3,517,669 | 6/1970 | Buono et al. | 604/119 |
| 3,527,478 | 9/1970 | Enssle | 285/38 |
| 4,182,385 | 1/1980 | Williamson | 604/902 |
| 4,369,991 | 1/1983 | Linder | 285/38 |
| 4,536,180 | 8/1985 | Johnson | 604/268 |
| 4,568,332 | 2/1986 | Shippert | 604/119 |

FOREIGN PATENT DOCUMENTS

| | | | |
|---|---|---|---|
| 106474 | 1/1939 | Australia | 604/241 |
| 2323925 | 11/1974 | Fed. Rep. of Germany | 128/229 |
| 3347834 | 4/1985 | Fed. Rep. of Germany | 604/119 |

Primary Examiner—John D. Yasko
Assistant Examiner—Colleen Reilly
Attorney, Agent, or Firm—Vorys, Sater, Seymour and Pease

[57] ABSTRACT

A surgical aspirator cannula including an elongated body having a distal end, a distal end port, a proximal end, a proximal end port and an aspirator conduit passing longitudinally therethrough. A cannula is removably secured to the distal end and when secured its cannula tip opening communicates through the cannula passageway with the distal end port. The proximal end of the body member is connected to a vacuum pump. A ball valve assembly is mounted in the body member in the aspiration conduit, and is operated by a hand-operated lever, knob or button supported on the body member. When the lever is then operated the valve assembly is selectively opened or closed to selectively communicate the source of vacuum with the distal end port and thus the cannula. The cannula has its proximal end fitted into a ferrule which fits into an adaptor that is screwed into the distal end portion of the body member. Then when the cannula nut is screwed onto the adaptor by twisting a cannula key fitted onto it, the ferrules will grip the cannula thereby securing it in place.

10 Claims, 4 Drawing Sheets

SURGICAL ASPIRATOR CANNULA

BACKGROUND OF THE INVENTION

The present invention relates to aspiration systems used in medical surgery and more particularly to those used for liposuction.

Surgical aspirator cannulas or vacuum curets have been used for many years to remove fluids and/or tissue from the body. They typically comprise a hollow tube or cannula having openings at each end with one opening attached to a source of vacuum. The opposite end is then introduced into that portion of the body from which the fluid and/or tissue is to be removed. Then when the vacuum is applied, the fluids and/or tissue are aspirated or sucked up through the opening in the opposite end and the hollow portion of the curet into a collecting container. These vacuum curets have been used in numerous medical procedures but more recently have been used in liposuction or lipexheresis. This technique has become widely accepted in the medical community and practiced by physicians of many different specialities to remove fat from all over the body. The body contains a limited number of fat cells which do not regenerate, and therefore when the fatty tissue is removed by liposuction the body part will be thinner. One widely practiced procedure is to remove an entire layer of regular deep fat to create a layer of space in the body which layer is then compressed to form the thinner body part.

Many surgical aspirator cannulas constructions are known, and they typically require that the cannula have a threaded distal end which then fits into a threaded nut at the distal end of the handle. This design is not adapted to provide an interchangeable cannula system but rather is constructed as the means by which the manufacturer assembles the cannula. In fact to to remove this cannula from the handle requires special tooling. Thus no cannula construction is known which provides for interchanging of different cannula configurations by the surgeon during the medical procedure. However, it is desired that differently configured cannulas be used during a single medical procedure in particular for liposuction in the upper torso. For this procedure different lengths and diameters of cannulas as well as differently configured tip shapes and openings are desired at different stages of the procedure. No aspirator cannula design is known which provides for the easy and quick interchangability of cannulas by the doctor during the medical procedure in a sterile environment.

Aspirator cannulas also are constructed so that the vacuum pump is connected through a hosing to the handle and the vacuum air passageway runs through the handle to the cannula. To connect or disconnect the vacuum with the cannula requires that a technician turn the vacuum pump off by switch means at the pump. This is inconvenient because the doctor cannot personally and directly control the application of the vacuum since the pump is not in a sterile environment. Further, because of the distance of the pump and pump hosing to the cannula tip a vacuum rise time of six to eight seconds is typical.

Accordingly, the primary object of the present invention is to provide an improved surgical aspirator cannula designed for surgical aspiration procedures and more particularly for liposuction.

Another object of the invention is to provide an improved surgical aspirator cannula design which allows for the easy and ready interchangability of different cannulas by the doctor during the aspirating procedure.

A further object of the present invention is to provide an improved surgical aspirator cannula design which reduces the vacuum rise time after the doctor has positioned the cannula in the wound and requests that the vacuum be applied to the cannula tip.

A still further object of the present invention is to provide an improved surgical aspirator cannula design which allows the doctor to personally, directly and conveniently control the application of the vacuum to the cannula tip.

Other objects and advantages of the present invention will become apparent to those persons having ordinary skill in the art to which the present invention pertains from the following description taken in conjunction with the accompanying drawings.

DETAILED DESCRIPTION OF THE PREFERRED EMBODIMENTS OF THE INVENTION

Figure 1:
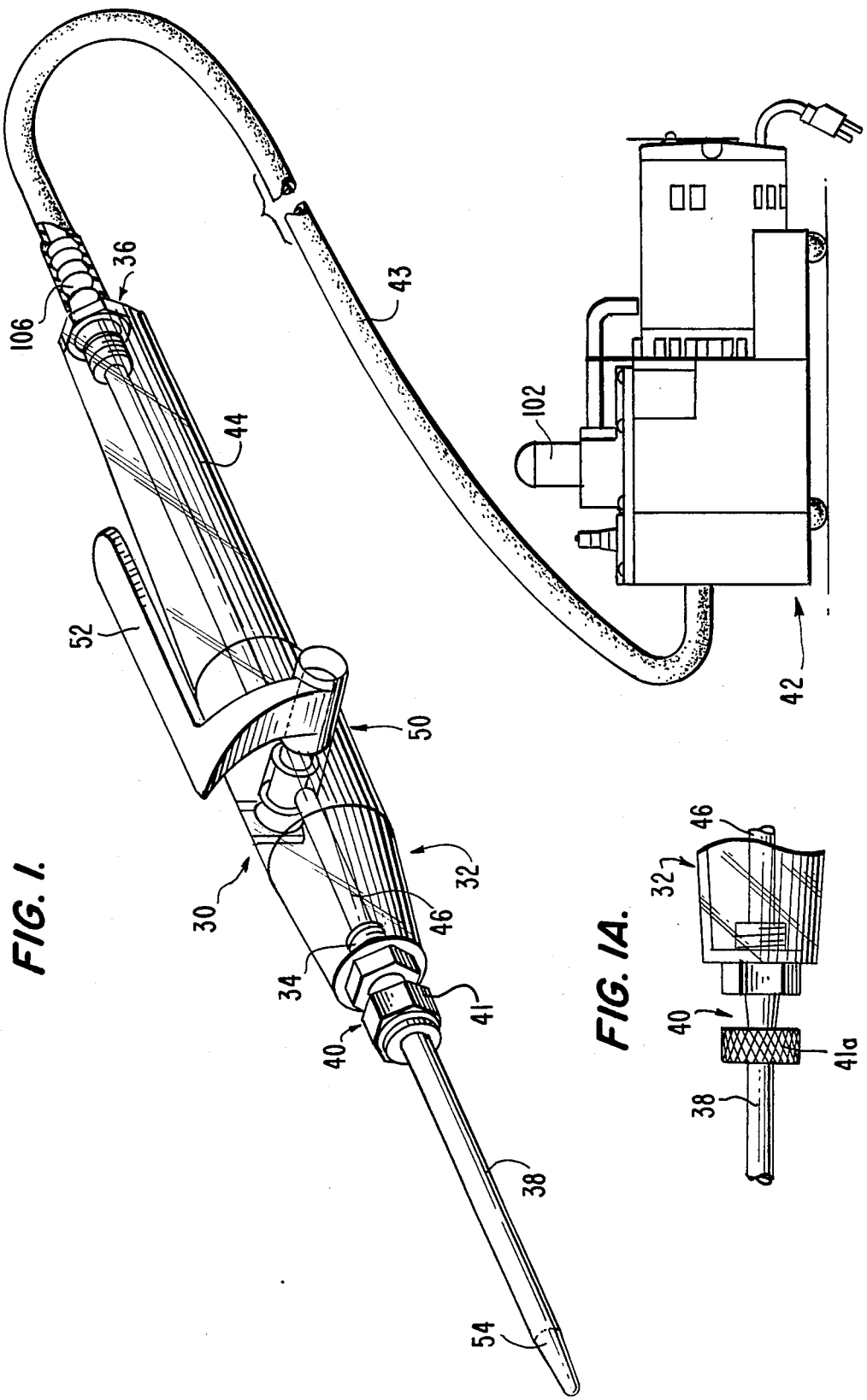
FIG. 1 is a perspective view of a surgical aspirator cannula of the present invention.

The surgical aspirator cannula of the present invention is illustrated generally at 30 in FIG. 1. It is seen to basically comprise a handle shown generally at 32 having a distal port 34, and a proximal port 36, a cannula 38 secured by a cannula connecting assembly shown generally at 40 to the distal end of the handle, a vacuum pump shown generally at 42 connected via a hosing 43 to the proximal end of the handle.

Figure 2:
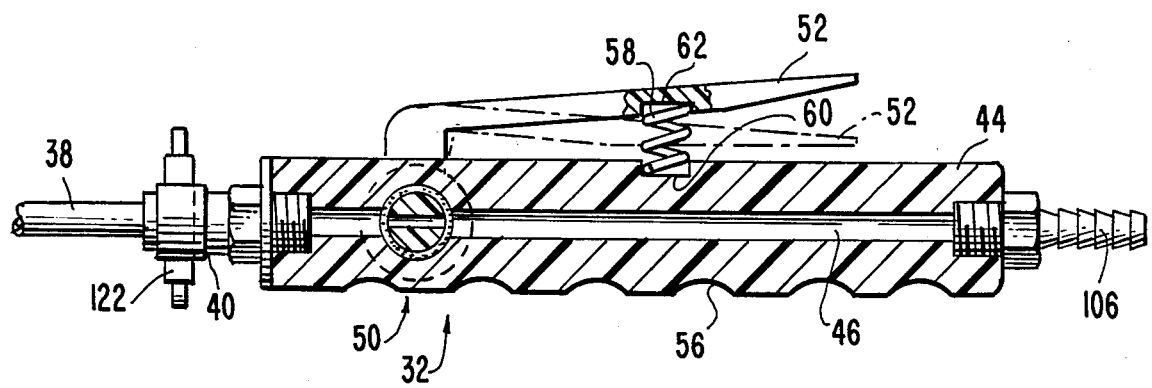
FIG. 2 is a side elevational view of the handle of the surgical aspirator cannula of FIG. 1 illustrating the operation of the hand operated lever.

Handle 32 is shown to include a body member 44 of a plastic material, such as Delrin, autoclavable at 270° Fahrenheit, formed in a slender elongated configuration and being about six inches long and one inch in diameter. An air passage or conduit 46 is provided extending longitudinally through it and communicating the distal and proximal ports 34, 36 of the body member. A valve assembly 50 is constructed in the body member 44 and intersecting the conduit 46, and is operable by a hand operated lever 52 movable between first and second positions. In the first position the conduit 46 is blocked such that the vacuum from the pump 42 does not communicate with the distal port 36 of the body member 44 and thus the cannula 38, and in the second position the conduit 46 is opened so that the vacuum can communicate with the distal port 34 and blood, tissue and the like can be aspirated through the tip opening 54 of the cannula when inserted into the body and through the conduit 46 to the pump 42. The lever 52 is configured in an L shape so as to be easily grasped by the surgeon's hand. When grasping the handle his fingers rest in finger grips or knurls 56 formed on the bottom surface of the body member 44, as best shown in FIG. 2. The lever 52 is normally biased in its "up" position by a bias spring 58, which is seated in a C-shaped groove 60 on the top surface of the body member 44 and similarly attached at the lower surface 62 of the lever 52. Bias spring 44 biases the lever 52 and thus the valve assembly 50 into the first position closing the conduit 46. Then when the surgeon desires to aspirate after positioning the cannula 38, he simply depresses the lever 52 and the conduit 46 is opened.

Figure 4:
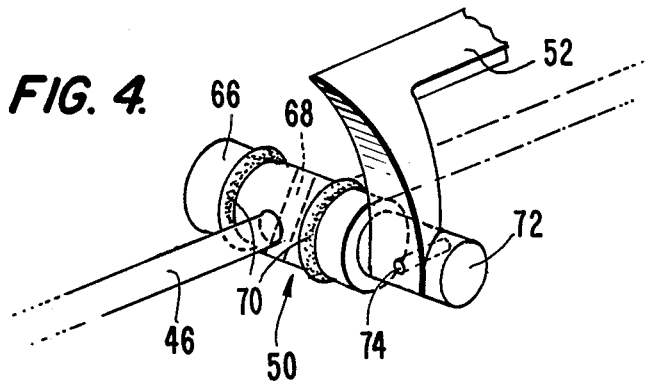
FIG. 4 is a perspective view of the valve assembly and lever of the handle of FIG. 2 shown in isolation for clarity's sake.
Figure 5:
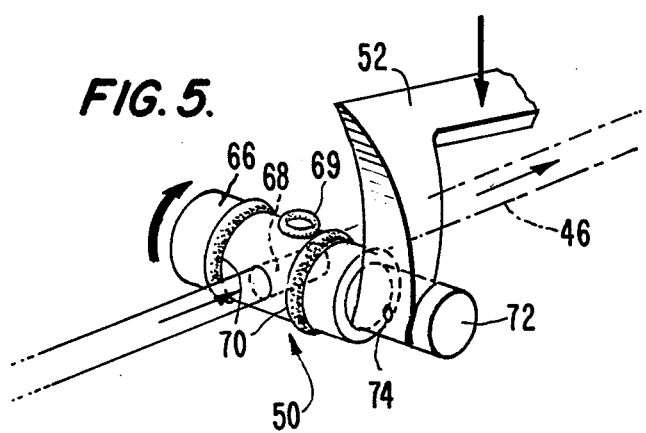
FIG. 5 is a view similar to FIG. 4 illustrating the valve assembly in the open position.

The operation of the valve assembly 50 is best illustrated in FIGS. 4 and 5. They show the valve assembly 50 to comprise a ball type valve wherein a cylinder 66 is provided disposed laterally through the body member 44. The cylinder 66 has an air passageway 68 extending laterally through it through its central portion. When the valve assembly 50 is in the first position, as illustrated in FIG. 4, the air passageway 68 does not communicate with the conduit 46 and thus air does not flow, but when the valve assembly 50 is moved to the second position as shown in FIG. 5 the air passageway 68 is aligned with the conduit 46 and air flows freely as indicated by the arrow in FIG. 5. A pair of O-rings 70 are providing encircling in cylinder 66 on opposite sides of the air passageway 68 to maintain an effective air seal and the cylinder 66 has an extension cylinder arm 72 extending out from the outer surface of the body member and to which the L shaped lever 52 is connected via a connector pin 74.

Figure 6:
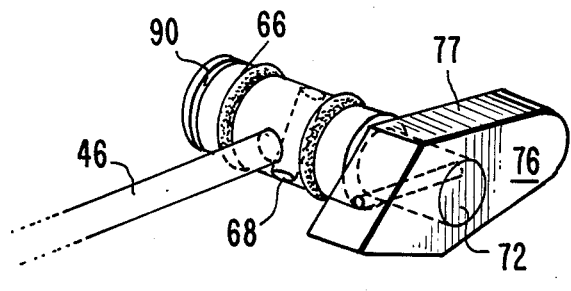
FIG. 6 is a view similar to FIG. 4 illustrating an alternative design for the lever for the valve assembly.
Figure 7:
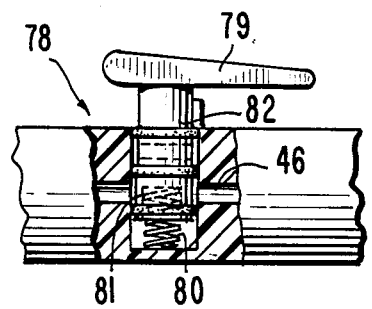
FIG. 7 is a side view of an alternative design for the valve assembly having portions thereof broken away for the sake of clarity.
Figure 8:
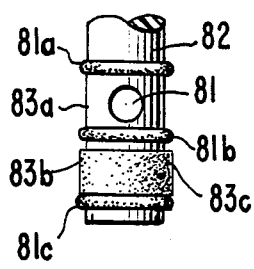
FIG. 8 is an enlarged fragmentary view of the cylinder of the valve assembly of FIG. 7.

An alternative design for the lever of the ball valve is illustrated in FIG. 6. As shown there, a rotating valve knob 76 is provided in lieu of the lever. Valve knob 76 is easily rotated between the first and second position by the surgeon's thumb engaging upper surface 77 as his hand grasps the body member.

Figure 9:
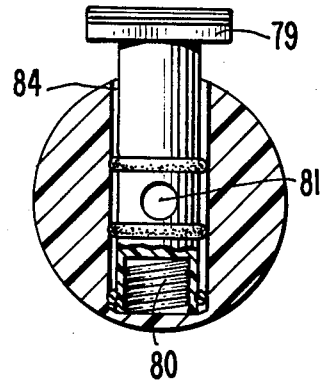
FIG. 9 is a cross-sectional view of the valve assembly of FIG. 7 illustrating the valve in the "open" position.
Figure 10:
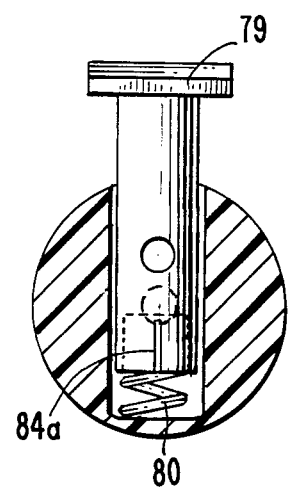
FIG. 10 is a view similar to FIG. 9 illustrating the valve in the "closed" position.

An alternative design of the valve assembly is illustrated in FIGS. 7-10 generally at 78. Valve assembly 78 is a push button design having a lever or push button 79 which operates against compression return spring 80 to position the passageway 81 so that it communicates with the conduit as in the "open" position of FIG. 9. O-rings 81a, b and c encircle ½ inch diameter cylinder 82 and define a flow cylinder area 83a over passageway 81 and between O-rings 81a and 81b and a no flow area 83b between O-rings 81b and c when in the closed position as illustrated in FIG. 10. An anti-rotation key 84 prevents cylinder 82 from rotating in its bore.

Figure 3:
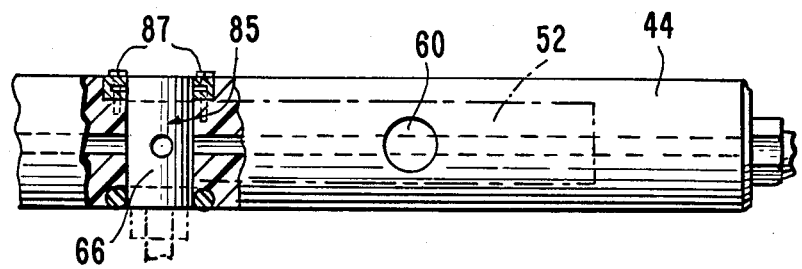
FIG. 3 is a fragmentary top plan view of the handle of FIG. 1 illustrating the ball valve seat assembly.
Figure 11:
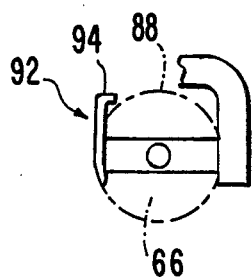
FIG. 11 is a view showing the valve assembly in isolation with an alternative means for locking the valve assembly in place in the body member.
Figure 12:
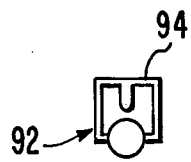
FIG. 12 is a front elevational view of the clip of the locking means of FIG. 11 illustrated in isolation.

The cylinder 66 of the valve assembly is installed and is held in position in the handle by means of a ball valve seat 85 as shown in FIG. 3. Seat 85 extends laterally through the handle and is formed of stainless steel tube 86 secured with three vlier screws 87 and four set screws positioned at 120°. An alternative design for a seating and retaining assembly for the valve assembly is shown in FIG. 11 wherein a channel 88 is formed laterally through the handle and the cylinder 66 positioned therein. The cylinder 66 is provided at its outer end with a circumferential groove 90 as shown in FIG. 6. A retaining clip 92 is inserted in this groove and when pressed down towards the body member the valve assembly 50 is locked in place and by simply raising the upper flange 94 of the clip 92 the valve assembly 50 is unlocked. The clip 92 is shown in front view in isolation in FIG. 8.

Thus, as can be appreciated, the vacuum pump 42 can be turned on and the ball valve assembly 50 will be in its normal first or closed position. The vacuum though extends all the way to the valve assembly quite near to the cannula 38. Then when it is desired to aspirate, the lever 52 is moved to its second or depressed position thereby opening the valve assembly 50 and the vacuum very quickly is released to the tip of the cannula 38. Because of the proximity of the valve assembly to the tip of the cannula there is virtually an instantaneous rise time for the vacuum thereby expediting the aspirating procedure. Also, it is less likely that the surgeon will move the cannula 38 out of alignment during this virtually instantaneous rise time after he has positioned it in position in the wound. It further does not require the constant presence of a technician to operate the nonsterile pump 42. The handle or lever 52 is formed of autoclavable materials and is always in the sterile environment and thus the switching mechanism for activating the vacuum is also within the sterile environment.

The pump 42 can be of any suitable design. One pump which can be used is the GAST single stage model 5BA-1-GF82X pump. This pump has a 100 milliliter or 3.5 cubic feet displacement and 29.99 inches of mercury. A filter 102 such as the "Coalescent Oil Removing Filter" manufactured by the Master Neumatic Detroit, Inc. can be installed on the exhaust port of the pump 42 to remove the oil mist so that bacteria does not escape into the surgical environment. Further, a filter such as a 0.1 micro in line filter can be added so that the fatty tissues which do not go into the trap of the pump will be contained. Hosing 43 connects operatively connects the vacuum pump 42 to the handle 32. A barbed hose fitting 106 at the proximal end of the body member is provided on which the hosing 43 is fitted and secured.

Figure 13:
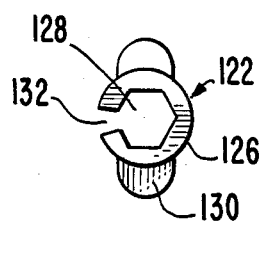
FIG. 13 is a front plan view illustrating in isolation the cannula key of FIG. 2.
Figure 14:
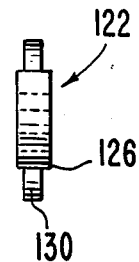
FIG. 14 is a side elevational view of the cannula key of FIG. 13.
Figure 15:
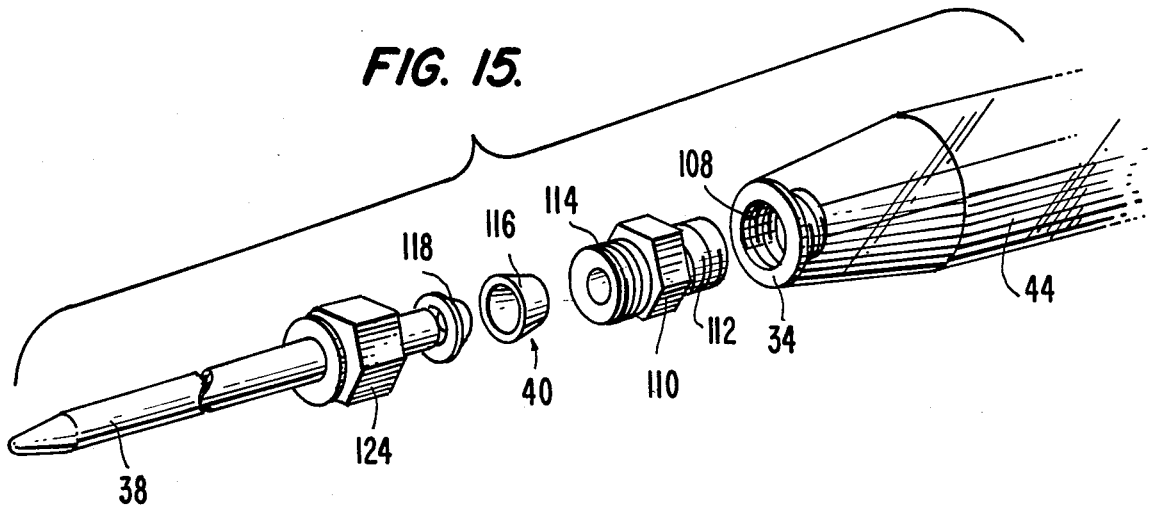
FIG. 15 is a perspective view of the cannula connecting means for the cannula of FIG. 1 wherein the components are illustrated in exploded relation.

The cannula connecting assembly 40 is best illustrated in FIG. 11. Referring thereto, it is seen that the distal end of the body member is provided with a threaded port 108. An adaptor 110 is provided having a threaded male member 112 at one end adapted to and threadably engaged in the distal port 108 and a threaded member 114 at its other end. A pair of interconnecting ferrules 116, 118 are provided, the proximal one 116 fits into the cone-shaped opening of the adaptor 110 and the distal ferrule 118 fits into the proximal ferrule 116 and also over the end of the cannula 38. When threaded into position as shown in FIG. 2, for example, the cannula key 122 is fitted over the cannula nut 124 and manually threaded to tighten the ferrules 116, 118 onto the smooth end of the cannula 38 and secure it in place. A novel cannula key 122 is best shown in FIGS. 13 and 14 and has a configuration including a circular body member 126 having a hexagonally configured opening 128 through it configured to engage over the hexagonal cannula nut 124. A pair of ears 130 are secured to the body member 126 at diagonally opposite locations and ears 130 are adapted to be grasped and rotated to tighten or loosen the nut 124 relative to the ferrules 116, 118. An opening 132 is provided through the body member 126 to the cannula key opening 128 as shown in FIG. 9. The key 122 is formed of a suitable autoclavable plastic material. The cannulas 38 then can be provided in a variety of configurations adapted to the different uses. These configurations include different lengths, diameters and tip configurations. The port opening configurations can be varied including the provision for a series of adjacent port openings. These differently configured cannulas are autoclaved and positioned to be easily accessed by the surgeon during the surgical procedure. Thus, by placing the cannula key 122 of the present invention over the cannula nut 124 and turning it, the cannula 38 is loosened first, then removed from its connection to the body member 126, and then another differently configured cannula 38 is inserted through the nut, the nut tightened by turning the cannula key and the new cannula thereby secured in position.

Figure 16:
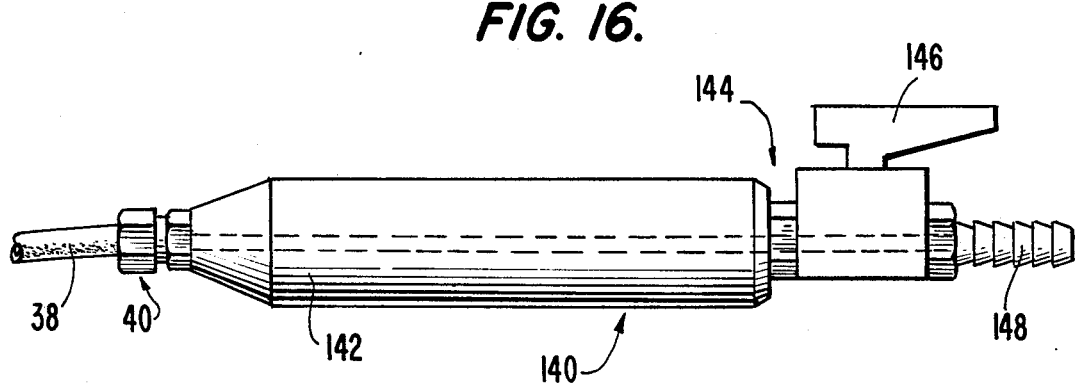
FIG. 16 is a side elevational view of an alternative handle design for the surgical aspirator cannula of the present invention.

An alternative design of the handle 140 of the present invention is illustrated in FIG. 16. As shown, the cannula connecting assembly 40 can be the same as that shown in FIG. 11, and the handle the body member 142 of the handle will be of conventional construction formed of autoclavable plastic and having the conduit extend all the way through. At the proximal end of the handle a select position ball valve 144 is provided which can be easily operated by the surgeon's hand as he holds the body member 142. Similar to the construction of valve assembly 50 of FIGS. 4, 5 and 6, the select position ball valve 144 will have open and closed positions and a lever 146 or other type of knob which can be physically moved to position the ball valve assembly in the desired position. A tubing barb 148 extends out from the select position ball valve 144 and the hosing 43 from the vacuum pump 42 connects onto it.

From the foregoing detailed description, it will be evident that there are a number of changes, adaptations, and modifications of the present invention which come within the province of those skilled in the art. However, it is intended that all such variations not departing from the spirit of the invention be considered as within the scope thereof as limited solely by the claims appended hereto.

What is claimed is:
1. A surgical aspirator cannula comprising:
an elongated body member having a distal end and a proximal end,
said body member defining an aspiration conduit passing therethrough generally between said distal and proximal ends,
said proximal end being operatively connectable to a source of vacuum,
said body member defining at said distal end a distal end port having a threaded opening,
a removable securing means for removably securing a proximal end of an elongated cannula to said distal end port so that a longitudinal passageway of the cannula which engages the cannula proximal end is in fluid communication with said aspiration conduit,
said securing means comprising an adaptor having distal and proximal threaded male connectors and a nut secured between them, and an adaptor passageway extending therethrough, said proximal threaded male connector threadably engaging in said threaded opening by rotating said adaptor nut relative to said body member, a ferrule means fitting in said distal threaded male connector, and a cannula nut positionable around the cannula and when tightened causing said ferrule means to grip the cannula end and thereby secure the cannula to said distal end, and
said ferrule means comprising a cone-shaped first ferrule fitting into said distal threaded male connector and a second ferrule fitting into said first ferrule and have a distal rim which said cannula nut engages.
2. The surgical aspirator cannula of claim 1 wherein said cannula nut has a multi-sided circumferential surface.
3. The surgical aspirator cannula of claim 2 wherein said securing means comprises a cannula key having a body portion with a multi-sided opening therethrough and a pair of ears projecting from said body portion, and said body portion fits around said cannula nut such that when rotated by grasping and turning said ears the surface of said multi-sided opening engages and turns said multi-sided circumferential surface.
4. The surgical aspirator cannula of claim 2 wherein said cannula nut threads onto said distal male connector.
5. The surgical aspirator cannula of claim 1 wherein the proximal portion of the cannula end has a generally smooth circumferential surface and fits into said ferrule means.
6. The surgical aspirator cannula of claim 1 further comprising a valve assembly positioned at least partially in said body member and in said aspiration conduit, and said valve assembly being positionable in a first valve position closing said conduit so that the source of vacuum is blocked relative to said distal end port, and in a second valve position opening said conduit so that the source of vacuum communicates with said distal end port.
7. The surgical aspirator cannula of claim 6 further comprising a hand-operated means supported by said body member and operatively connected to said valve assembly for moving said valve assembly between said first and second valve positions.
8. The surgical aspirator cannula of claim 7 wherein said hand-operated means includes a lever supported by said body member, and a biasing means for biasing said lever.
9. The surgical aspirator cannula of claim 1 wherein said aspiration conduit defines a straight line between said distal and proximal ends and through said body
10. The surgical aspirator cannula of claim 1 wherein said cannula nut threads onto said distal male connector.

* * * * *